United States Patent
Iafrati et al.

[11] Patent Number: 6,129,661
[45] Date of Patent: Oct. 10, 2000

[54] ENDOSCOPIC INSTRUMENTATION WITH WORKING CHANNEL

[75] Inventors: Mark Iafrati, Potomac, Md.; Gheorghe Mihalca, North Chelmsford, Mass.

[73] Assignee: Smith & Nephew, Inc., Memphis, Tenn.

[21] Appl. No.: 09/057,952

[22] Filed: Apr. 9, 1998

[51] Int. Cl.[7] .................................. A61B 1/012
[52] U.S. Cl. .................. 600/121; 600/114; 600/125; 600/131; 600/153; 606/159
[58] Field of Search .................. 600/105, 114, 600/121, 123, 125, 128, 131, 136, 153, 164, 186, 188, 190, 199, 200; 606/159

[56] References Cited

U.S. PATENT DOCUMENTS

| | | | |
|---|---|---|---|
| Re. 32,158 | 5/1986 | Vukovic | 600/123 |
| 2,120,996 | 6/1938 | Wappler | 600/128 |
| 2,990,830 | 7/1961 | Hett | 670/163 |
| 3,261,350 | 7/1966 | Wallace | 600/128 |
| 4,306,547 | 12/1981 | Lowell | 600/188 |
| 4,392,485 | 7/1983 | Hiltebrandt | 600/153 |
| 4,606,330 | 8/1986 | Bonnet | 600/128 |
| 4,610,242 | 9/1986 | Santangelo | 600/114 |
| 4,630,598 | 12/1986 | Bonnet | 600/128 |
| 4,653,476 | 3/1987 | Bonnet | 600/153 |
| 5,048,508 | 9/1991 | Storz | 600/164 |
| 5,263,472 | 11/1993 | Ough | 600/188 |
| 5,373,840 | 12/1994 | Knighton . | |
| 5,400,768 | 3/1995 | McNamara et al. | 600/114 |
| 5,486,155 | 1/1996 | Muller et al. | 600/105 |
| 5,569,291 | 10/1996 | Privitera et al. . | |
| 5,571,172 | 11/1996 | Chin . | |
| 5,591,183 | 1/1997 | Chin . | |
| 5,593,418 | 1/1997 | Mollenauer . | |
| 5,601,581 | 2/1997 | Fogarty et al. . | |
| 5,601,589 | 2/1997 | Fogarty et al. . | |
| 5,667,475 | 9/1997 | Laser et al. | 600/128 |
| 5,667,480 | 9/1997 | Knight et al. | 606/159 |
| 5,695,448 | 12/1997 | Kimura et al. | 600/114 |
| 5,876,329 | 3/1999 | Harhen | 600/121 |
| 5,891,013 | 4/1999 | Thompson | 600/114 |

FOREIGN PATENT DOCUMENTS

| | | |
|---|---|---|
| WO 95/14425 | 6/1995 | WIPO . |
| WO 96/36388 | 11/1996 | WIPO . |
| WO 97/21398 | 6/1997 | WIPO . |

OTHER PUBLICATIONS

Iafrati et al., "Subfacial endoscopic perforator ligation: An analysis of early clinical outcomes and cost", Abstract, Journal of Vascular Surgery Abstracts, Jun. 1997, vol. 25, No. 6.

Endoscopic Saphenous Vein Harvesting, Brochure, Karl Storz Endoscope online, 4 pages.

*Primary Examiner*—John P. Leubecker
*Attorney, Agent, or Firm*—Fish & Richardson P.C.

[57] ABSTRACT

An endoscope includes a housing having a working channel extending therethrough; an elongated insertion section mounted to the housing and having a distal end to be attached on the housing so as to cover a portion of the elongated insertion section. The sheath creates and maintains a working space at the surgical site.

25 Claims, 7 Drawing Sheets

ENDOSCOPIC INSTRUMENTATION WITH WORKING CHANNEL

BACKGROUND OF THE INVENTION

The Invention Relates to Endoscopes.

Surgical procedures for treating incompetent perforating veins and for harvesting saphenous veins generally require long incisions to be made along the leg of the patient.

Perforating veins run substantially perpendicularly through layers of subcutaneous fat and muscle fascia (i.e., the fibrous layer attached to underlying softer tissue) into the muscle to connect the deep and superficial venous systems. When the perforating veins become diseased (e.g., varicose), it may be necessary to surgically remove portions of the vein, or strip out the entire vein. In milder cases, merely tying off (ligate) the veins to relieve pressure may suffice.

One conventional approach for ablating such perforating veins in the leg is to make a relatively long incision extending from the knee down to below the ankle. However, patients having incompetent perforating veins (particularly the elderly) may suffer from chronic venous insufficiency (CVI), a condition in which the skin becomes ulcerated and often infected. Incisions made through skin in this condition have a relatively high wound complication rate. At best, patient recovery is significantly increased and, in some cases, a new, morbid wound is created.

Saphenous vein harvesting is typically performed in conjunction with coronary (heart) or peripheral artery bypass. Under endoscopic visualization, the saphenous vein is harvested from the leg and used to bypass a clogged artery in the heart or leg. In conventional approaches for removing the saphenous vein, a single long incision or several separate and spaced incisions are made along the length of the leg. The vein is then freed by severing and ligating the branches of the vein, after which the vein is removed from the patient. The single long incision or series of spaced incisions is then closed using, for example, suture or stapes.

A new approach, known as subfascial endoscopic perforator surgery (SEPS), has recently developed as an alternative procedure for performing perforator ligation. In general, the SEPS procedure allows a working instrument to be introduced through a small incision and, with the aid of an endoscope, guided below the fascia to the surgical work area. This is particularly advantageous for patients suffering from chronic venous insufficiency since the SEPS approach allows incisions to be made in healthy tissue remote from the morbid tissue; one incision is generally required for the working instrument, another for the endoscope used to visualize the procedure. Thus, the SEPS approach reduces wound complications often associated with procedures involving long incisions through compromised tissue.

SUMMARY OF THE INVENTION

The invention features an endoscope having a working channel through which a working instrument is introduced for use at a worksite, and a detachable sheath for creating and maintaining a working space for the working instrument at the worksite.

In a general aspect of the invention, the endoscope includes a housing having the working channel extending therethrough; an elongated insertion section, mounted to the housing and having a distal end for insertion into an object; and a sheath configured to be attached to the housing so as to extend along the optical axis of the endoscope and cover a portion of the elongated insertion section. The sheath defines a working space that communicates with the working channel of the housing.

Thus, the endoscope provides visualization of a surgical site while facilitating access for handheld surgical instruments to the site through the working space. The endoscope is adapted to receive one or more multipurpose detachable sheaths. The sheaths primarily create and maintain a working space at the surgical site to improve visualization by the endoscope. The sheaths also protect the elongated insertion section of the endoscope and the surgical instrument extending therethrough. In certain applications the sheaths may be used to perform limited dissection of tissue.

Because no two patients and procedures are identical, the sheaths used with the endoscope are of different sizes and shapes. Thus, a family of reusable instruments is provided, each instrument being easily attachable and detachable from the endoscope and individually constructed for use in a particular anatomical situation. Advantageously, only a single incision is required for providing access to the surgical worksite for the working instrument and visualization of the worksite by the endoscope.

Embodiments of the invention may include one or more of the following features.

A distal end of the sheath is sized and shaped to temporarily displace portions of the object (e.g., tissue) when inserted therein. For example, the distal end has a radius of curvature relative to the optical axis of the sheath which is greater than a radius of curvature of an elongated shaft portion of the sheath. In one embodiment, the distal end extends outwardly away from the optical axis.

In certain embodiments, the detachable sheath has an open medial portion, extending substantially the length of the sheath, allowing greater maneuverability of the surgical instrument and reducing trauma to the tissue during its introduction through tissue. The opening defines a wall having in cross-section a C-shape. Alternatively, in other embodiments, the detachable sheath has a closed medial section forming a tube to enclose the elongated insertion section, thereby creating a sealed working space for procedures requiring gas insufflation.

The endoscopic instrumentation system utilizes a combination of a tapered mount with a bayonet locking mechanism to mechanically couple the housing and detachable sheath. In particular, the distal end of the housing has a tapered outer surface which mates with a corresponding tapered inner surface of the proximal end of the sheath. This mounting arrangement is mechanically robust and provides a quick and reliable approach for attaching and detaching the sheaths from the endoscope. Where gas insufflation is required, an airtight sealing ring can be provided between the housing of the endoscope and the detachable sheath.

The endoscope includes a handle connected to the housing and extending in a direction offset from the optical axis defined by the elongated insertion section. In certain embodiments, the handle extends in a direction substantially transverse to the optical axis. offsetting the handle in this manner provides an unobstructed space which is in-line with the longitudinal axis of the insertion section, thereby facilitating manipulation of the surgical instruments introduced through the working channel of the endoscope.

The elongated insertion section and handle of the endoscope includes an optical system. The handle includes a rotatable manipulator coupled to a mechanism for focusing the optical system. With this arrangement, the endoscope is easily rotated about the optical axis of the endoscope without cables and working instruments used with the endoscope becoming entangled. In addition, this arrangement allows the surgeon to hold and manipulate (e.g., reposition and focus) the endoscope with one hand while freeing the use of the other hand for manipulating the working instrument.

During manipulation of the endoscope and working instruments extending therethrough, significant forces can be imparted both longitudinally and radially to the distal end of the sheath. The rugged construction of the sheaths and the manner in which the sheath is mounted to the endoscope avoids bending to reduce the risk of impingement on the elongated insertion section with its optical elements and working instrument.

The working channel has an exit port having, in cross section, a semi-circular (sector or pie-shaped) opening to increase lateral movement of the working instrument passing therethrough. The elongated insertion section includes light transmissive elements (e.g. a fiber optic bundle) for conveying light from an external light source to the object. The housing further includes an insufflation port which, when used with a closed sheath, permits delivery of gas or fluid insufflation to the worksite.

Another aspect of the invention relates to a method of visualizing a surgical procedure on a body using an endoscope of the type described above. The method includes attaching a sheath on the housing to extend generally along and in parallel with the optical axis to cover a portion of the elongated insertion section; positioning the insertion section and sheath through an incision port in the body and to a surgical worksite; and introducing a working instrument to the surgical worksite through the working channel of the housing. The sheath defines a working space that communicates with the working channel of the housing.

Embodiments of this aspect of the invention may include one or more of the following features.

Positioning the insertion section and sheath includes manipulating a handle which is attached to the housing and extends in a direction substantially transverse to the optical axis of the endoscope. The handle is manipulated by the user using one hand while the working instrument is introduced using the other hand. The endoscope is focused by actuating a focusing mechanism disposed on the handle.

The method further includes introducing gas insufflation to the surgical worksite.

Other features and advantages of the invention will become apparent from the following detailed description, and from the claims.

DETAILED DESCRIPTION

Figure 1:
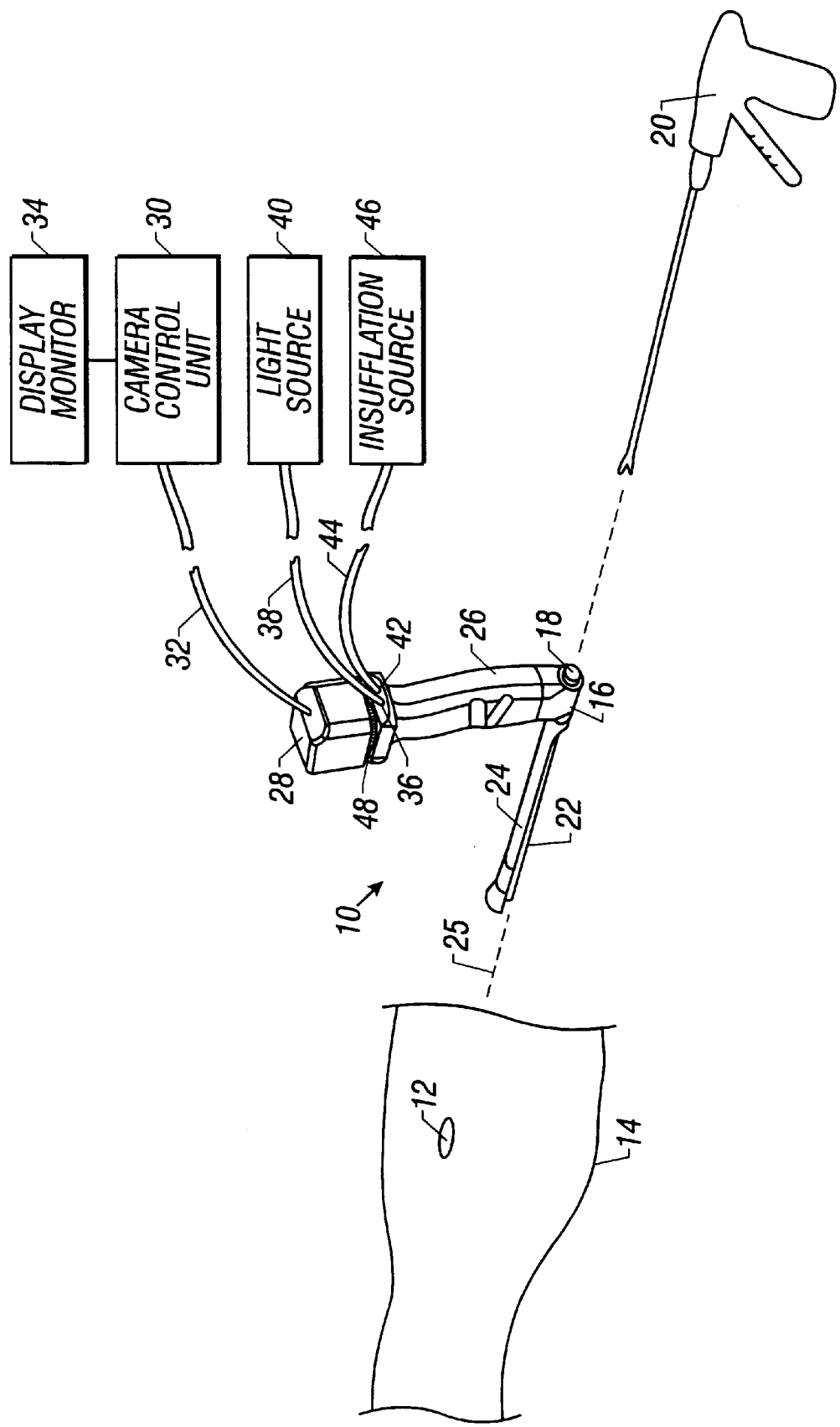
FIG. 1 shows an endoscope according to the invention and a handheld instrument positioned for use in a surgical procedure.

Referring to FIG. 1, a video endoscope 10 is shown prior to being inserted within an incision port 12 in the body, here a leg 14 of a patient. Endoscope 10 is of the type including an optical system (described in detail below) for conveying an optical image from a distal end of the endoscope to a video camera 28 attached to the endoscope.

Figure 2:
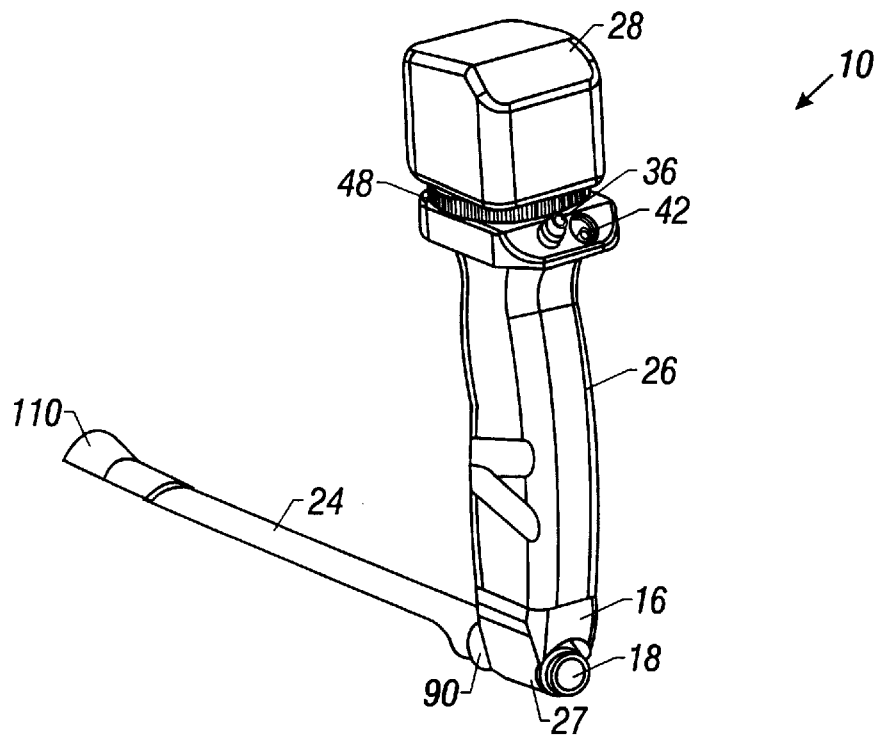
FIG. 2 is a rear perspective view of the endoscope of FIG. 1.
Figure 3:
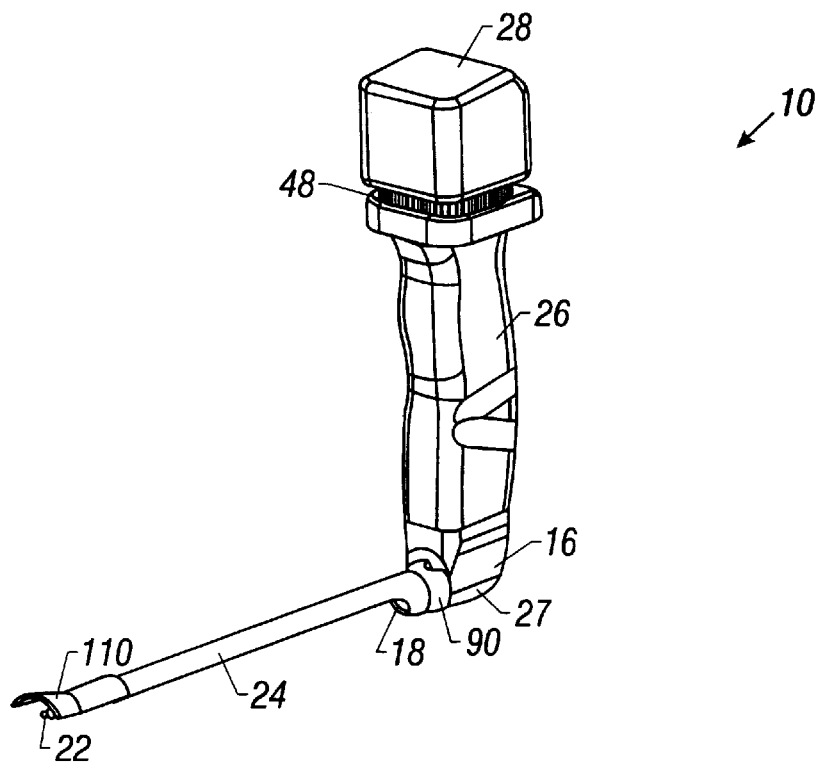
FIG. 3 is a front perspective view of the endoscope of FIG. 1.

Referring also to FIGS. 2–3, endoscope 10 includes a housing 16 having a working channel 18 for allowing a handheld instrument 20 (e.g., ligator. dissector, cutter, abrader) to extend through the housing for use in a surgical procedure being viewed with endoscope 10. An elongated insertion section 22 (which defines an optical axis 25 of the endoscope) and a detachable sheath 24 extend from housing 16.

As will be described in greater detail below in conjunction with FIG. 9, endoscope 10 can be used with any of a family of detachable sheaths, each of which is sized and shaped to create and maintain a working space at a surgical worksite for working instruments introduced through working channel 18 of housing 16. Each detachable sheath 24 also serves to protect elongated insertion section 22, particularly during advancement through tissue.

A handle 26 for manipulating endoscope 10 extends in a direction substantially perpendicular to optical axis 25 to provide an unobstructed space, in-line with optical axis 25 of the endoscope, thereby facilitating manipulation of surgical instruments introduced through working channel 18. In addition, a rounded heel region 27 of handle 26 has a low profile to facilitate introduction and manipulation of a second working instrument within incision port 12 but beneath insertion section 22. A video camera 28 having an electro-optical sensor (not shown) is mounted to the upper end of handle 26. The electro-optical sensor may be, for example, a charge-coupled device (CCD) for converting optical images received by the endoscope to electrical image signals.

Electrical image signals from video camera 28 are conveyed to a camera control unit 30, via a cable 32, for view on a display monitor, such as color CRT 34. The upper end of handle 26 also includes a fitting 36 (FIG. 2) which receives a fiber optic cable 38 connected to a light source 40. A second fitting 42 (FIG. 2), adjacent fitting 36, receives a tube 44 connected to a gas (e.g., $CO_2$) or fluid insufflation source 46. As will be described in greater detail below, gas provided to fitting 36 is passed to the surgical worksite through handle 26, housing 16 and a cylindrically-shaped closed sheath. A focusing ring 48 is positioned at the upper end of handle 26 to allow the user to focus endoscope 10. This arrangement provides several advantages. Arranging handle 16 to be offset from optical axis 25 provides an unobstructed space for manipulating handheld instrument 20. Attachments to endoscope 10 are also located away from optical axis 25 so that the surgeon can manipulate the endoscope and working instruments extending therethrough without interference from cables 32, 38, 44. Further, because the optical, illumination and gas insufflation systems are all arranged along the same plane of handle 16, endoscope 10 can be easily rotated around optical axis 25 without the cables becoming entangled with each other or any working instruments used with the endoscope. Further still, the contour of handle 26 allows its use by a surgeon with either hand (i.e., left to right or vice versa).

Figure 4:
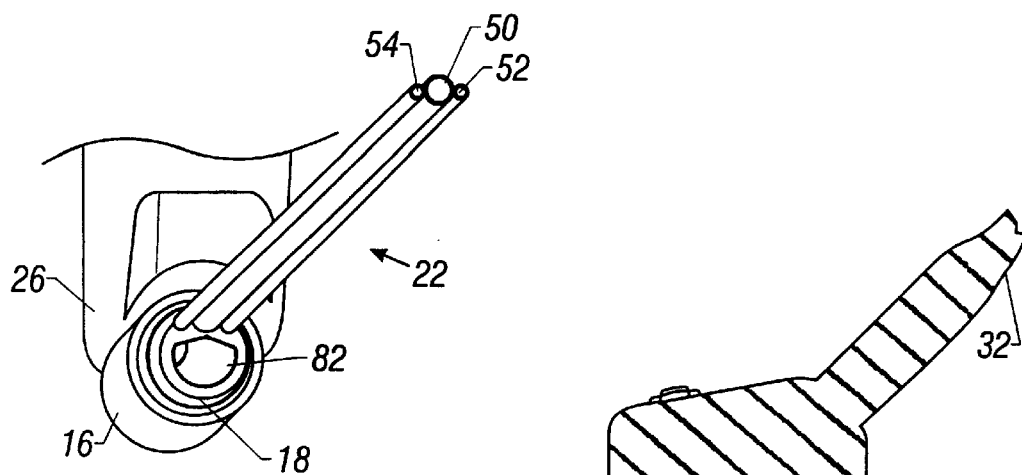
FIG. 4 is a front perspective view of a housing of the endoscope of FIG. 1.

Referring to FIG. 4, insertion section 22 is shown with sheath 24 removed to reveal an optical support tube 50 disposed between a pair of illumination support tubes 52, 54. Each tube has a length of approximately 230 mm. Fiber optic bundles 55 (FIG. 7) are positioned within and extend the length of support tubes 52, 54, and through housing 16 to fitting 36 on handle 26.

Figure 5:
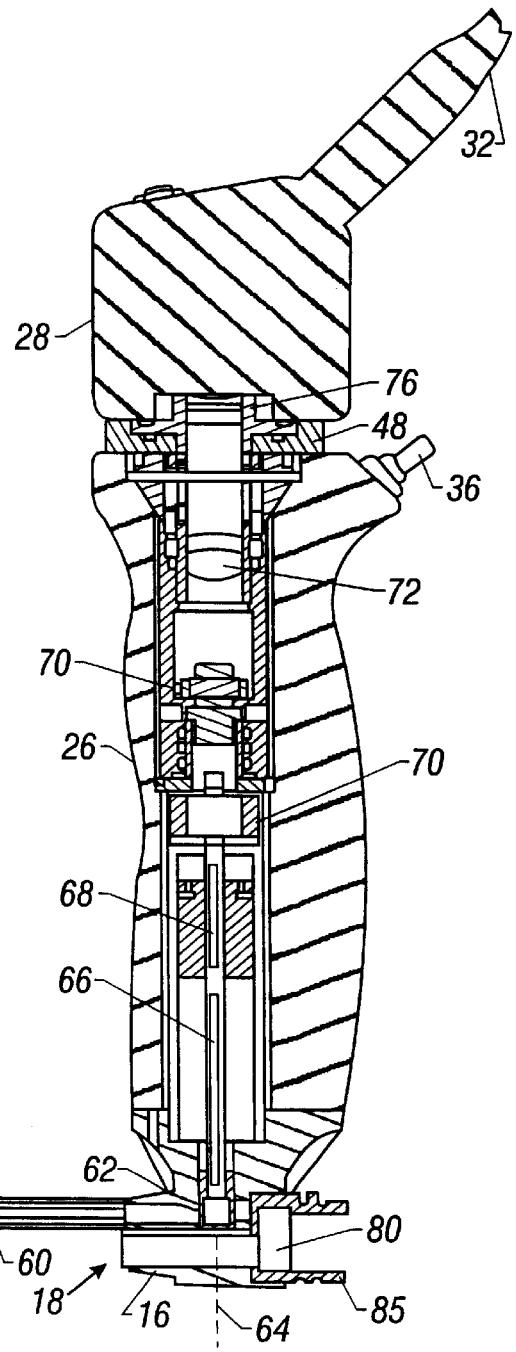
FIG. 5 is a cross-sectional side view of the endoscope of FIG. 1.
Figure 5:
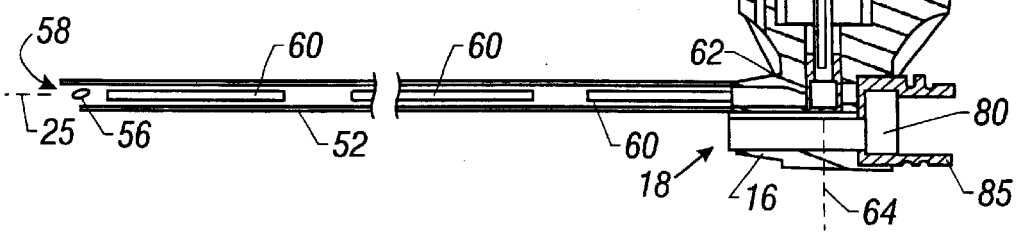

Referring to FIG. 5, an objective lens assembly 56 is disposed within a distal end 58 of optical support tube 50 to receive and convey the image of the object being viewed to a series of relay lens systems 60 within the support tube. Objective lens assembly 56 is positioned within distal end 58 to provide a direction of view pointing downward toward the open portion of the sheath and at an angle of about 12 degrees from optical axis 25. For this reason, distal 58 of support tube 50 is bevelled to hood objective lens system 60 and provides an unobstructed view of the worksite. Objective lens assembly 56 provides a field of view of about 85 degrees.

With a detachable sheath of the type shown in FIGS. 1–3, the range of movement at the distal end of a working instrument passing through endoscope 10 is substantial (e.g., as much as 2 inches). However, because the view provided by objective lens assembly 56 is directed slightly downward, if endoscope 10 is required to be moved at all, it is most likely moved so that the distal end tilts upwardly, consistent with the direction endoscope 10 tilts due to its own weight and the weight of cables 32, 38, 44.

Relay lens systems 60 convey images to a prism 62, positioned within housing 16, which translates the image to an axis 64 defined by handle 26. In particular, the image is received by a series of a relay lenses 66 disposed within a vertical tube 68 within handle 26. An ocular lens 70 is positioned at the proximal end of vertical tube 68 to receive and convey the image to a focusing lens 72. Focusing lens 72 is supported within a sleeve 74 mechanically coupled to focusing ring 48 which, when rotated, moves focusing lens 72 along axis 64 of handle 16. An endoscope mechanism suitable for use in endoscope 10 is described in U.S. Pat. No. 5,575,757, entitled "Endoscope with Focusing Mechanism", assigned to the assignee of the present invention and incorporated herein by reference. Handle 26 includes, at its proximal end, a centering mount ring 76 for receiving video camera 28.

Referring again to FIG. 4, as well as FIGS. 6–7, working channel 18 is positioned adjacently below optical support tube 50 and illumination support tubes 52. Working channel 18 has a working length between about 200 and 230 mm and a diameter in a range between about 5.5 mm and 7 mm for an endoscope 10 having an insertion section with a diameter between 10 and 14 mm. A working channel of this dimension is sufficiently sized to receive handheld working instruments having shafts of 5 to 6 mm diameter. Working channel 18 includes a sector or pie-shaped port 80 (FIG. 5) to allow greater side-to-side maneuverability of instruments used through the working channel. Due to the shape of port 80 and the length of the insertion section 22, a relatively small movement of working instrument 20 at the proximal end of endoscope translates to a much larger movement at the worksite, with sheath 24 providing better visibility by moving tissue away.

Figure 6:
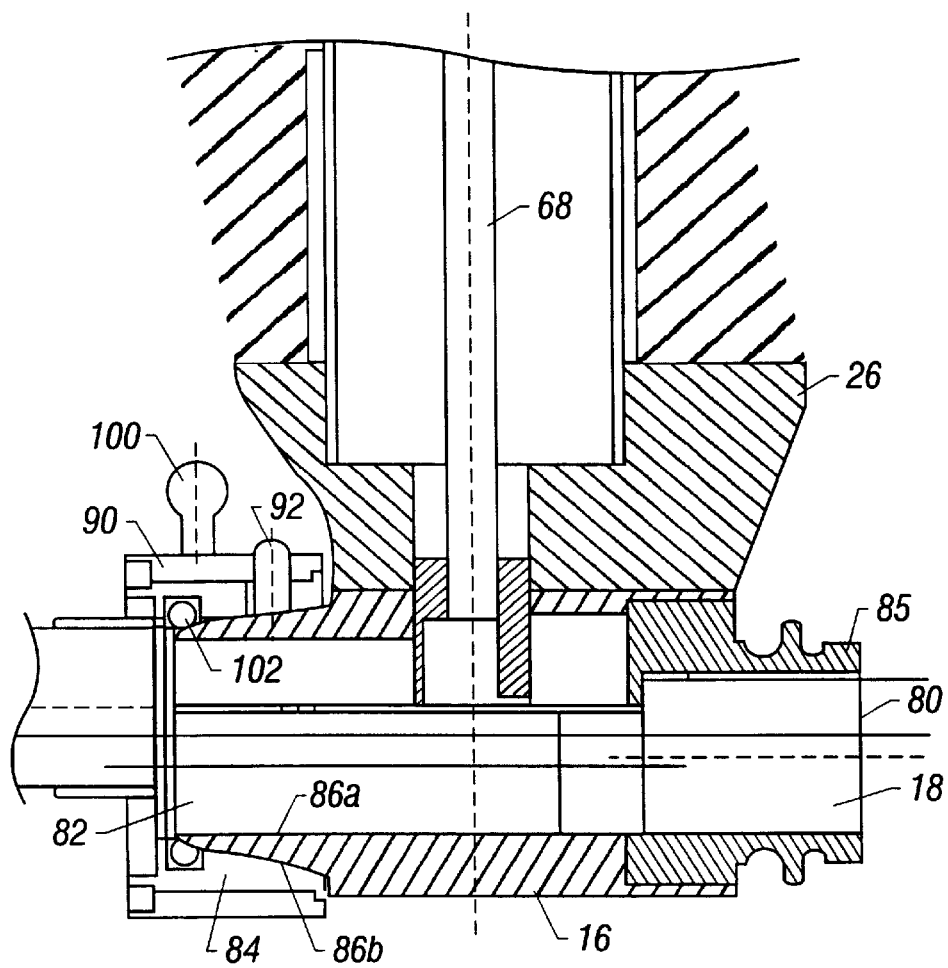
FIG. 6 is a cross-sectional side view of the housing of the endoscope of FIG. 1.
Figure 7:
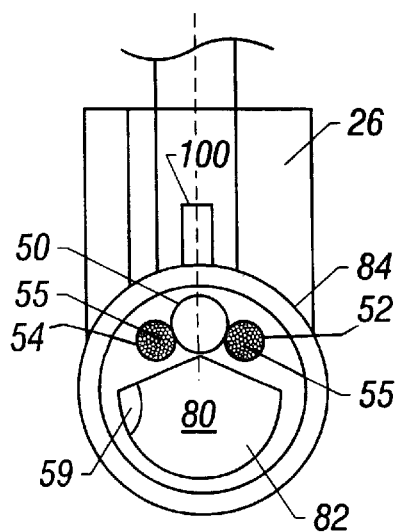
FIG. 7 is a front view of the housing of the endoscope having an insufflation channel.

Referring to FIG. 6, housing 16 includes a distal end 84 having a tapering outer surface 86a for mating with a corresponding tapering inner surface 86b of a locking ring 90. Locking ring 90 is attached to and rotates freely about the proximal end of detachable sheath 24. In one embodiment, outer surface 86a is tapered relative to optical axis 25 at an angle of about 8 degrees.

For applications requiring gas insufflation, housing 16 also includes a gas port 59 (FIG. 7) which connects to a conduit (not shown) extending through handle 26 to fitting 36. As will be discussed in greater detail below, when a cylindrical detachable sheath 24e (FIG. 9.) is attached to distal end 84 of housing 16, gas insufflation flows to the surgical worksite through gas port 59 and along the length of sheath 24e. Because sheath 24e is "closed" (i.e., does not have an open side wall) it serves as a conduit between gas port 59 and the surgical worksite. In such applications, a fitting 85 is shown permanently attached to entrance port 80 for receiving a gas seal member 81 (FIG. 11) to provide an air-tight seal between a working instrument passing through working channel 18.

Figure 8:
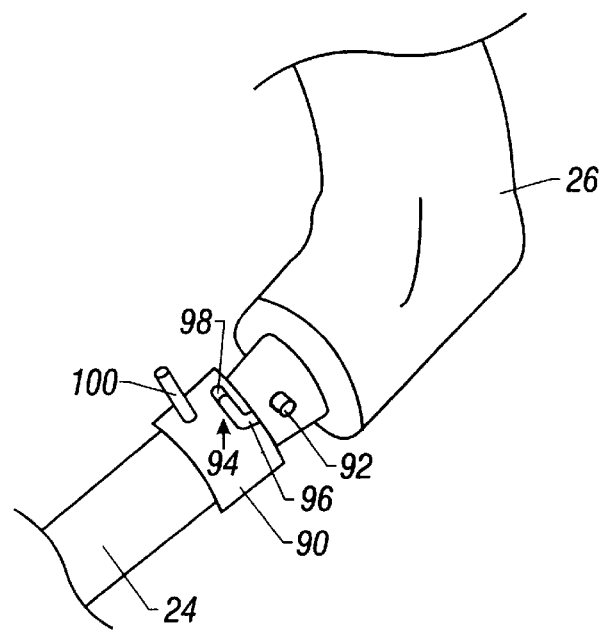
FIG. 8 is a perspective view of the bayonet mount used to attach the interchangeable sheath to the endoscope.

Referring to FIG. 8, the coupling between detachable sheath 24 and housing 16 is accomplished using a bayonet mount. In particular, a pin 92 projects upwardly from outer surface 86a of housing 16 and is received within an L-shaped slot 94 of locking ring 90. L-shaped slot 94 includes a longitudinal groove 96 terminating at a groove 98. To lock detachable sheath 24 to housing 16, pin 92 is slid within longitudinal groove 96 until it reaches groove 98. A projecting stem 100 formed on locking ring 90 is then rotated counterclockwise to draw surfaces 86a, 86b of respective ones of housing 16 and locking ring 90 together in a self-locking manner. The bayonet mount also includes an O-ring 102 (FIG. 6) to seal the interface between housing 16 and sheath 24 in the event that gas insufflation is required.

Figure 9:
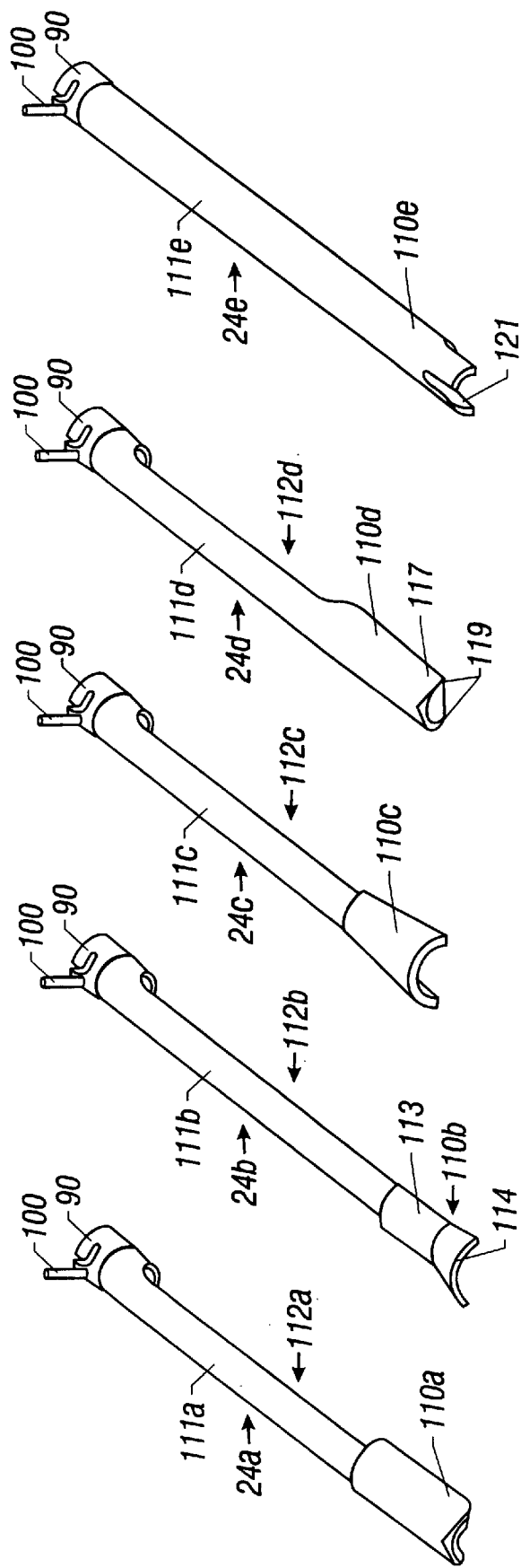
FIG. 9 is a perspective view of a family of interchangeable sheaths for use with the endoscope of FIG. 1.

FIG. 9 shows an exemplary set of detachable sheaths 24a–24e, each being approximately 230 mm in length and having shafts 111a–111e extending between locking ring 90 and corresponding distal end members 110a–110e. The shafts 111a–111d of some of the sheaths 24a–24d are open. By "open" it is meant that shafts 111a–111d have C-shaped walls (in cross section) which define open sides 112a–112d and extend over a predetermined arc of curvature along substantially the entire length of the sheaths. In contrast, "closed" in this context means that shaft forms a complete tube. For example, sheath 24e has a closed tube-like shaft 111a having a distal end member 110e with a C-shaped open wall. Of course, all sheaths 24a–24e have open distal ends, as shown in FIG. 9.

In general, because shafts 111a–111d include open sides 112a–112d pressure and trauma inflicted upon the surrounding anatomy is minimized as endoscope 10 and sheath 24 are advanced through tissue. Sheaths 24a–24d with open sides 112a–112d are particularly well-suited in procedures in which more than one handheld instrument is being used as the same time. For example, one handheld instrument is used through the sheath while the other instrument is used along side the sheath. Open sides 112a–112d also permit a larger range of movement (particularly lateral movement) of handheld instruments introduced through working channel 18 and hooded by the sheaths.

In general, each of open sheaths 24a–24d include distal end members 110a–110d shaped to create and maintain a working space at the surgical site. Specifically, distal end members 110a–110c are shaped with radii of curvature greater than that of shafts 111a–111c. The larger radii of distal end members 110a–110c serve to push surrounding tissue away at the distal end of the sheaths, thereby creating an expanded working space. However, distal end members 110a–110d are sized and configured differently to adapt to anatomical differences between patients as well as the particular worksite within a patient.

For example, distal end member 110a is cylindrically shaped and extends coaxially and in parallel with shaft 111a a distance of approximately 50 mm from the tip of sheath 24a.

Sheath 24b and sheath 24c are particularly well-suited for surgical procedures involving the lower leg or thigh because each sheath maintains a working channel generally parallel with the leg while providing an exposed, fuller view at the distal end of each sheath. Distal end member 110b of sheath 24b has a cylindrically shaped proximal portion 113 which extends distally and in parallel with shaft 111b and then flares outwardly to provide an enlarged working space.

Figure 10A:
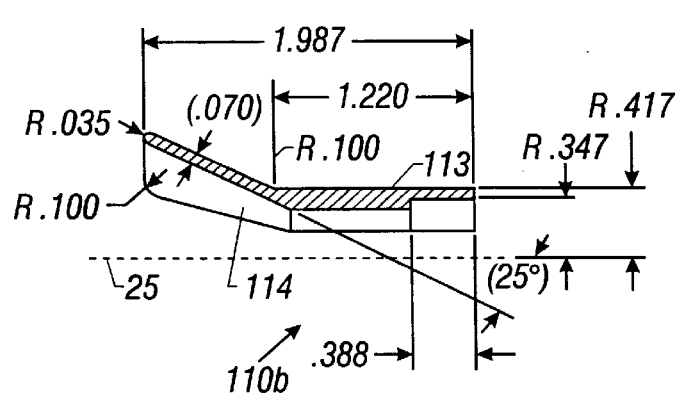
FIGS. 10A and 10B are cross-sectional side and front views, respectively, of the distal end of one of the interchangeable sheaths of FIG. 9.
Figure 10B:
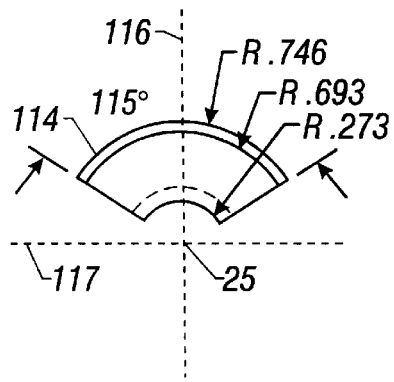

Referring to FIGS. 10A–10B, outwardly flaring distal end member 110b has a length of about 0.75 inches and extends outwardly, relative to optical axis 25, at an angle of 25 degrees. End portion 114, in cross-section, extends about 58 degrees to either side of a vertical plane 116 passing through optical axis 25 and perpendicular to a horizontal axis 117. With this configuration, a working instrument passed through working channel 18 and hooded by sheath 24 is capable of being maneuvered at the distal end of the sheath by as much as 1 inch to either side of plane 116.

Referring again to FIG. 9, distal end member 110c has a shape which gradually tapers outwardly from a proximal end to a distal end. Sheath 24d, on the other hand, has an integrally formed distal end member 110d which is not enlarged (i.e., distal end member has the same radius of curvature as shaft 111d). Distal end member 110d has a C-shaped wall 117 (in cross-section) similar to that of shaft 111d, but having a smaller opening between edges 119 defining C-shaped wall 117. C-shaped wall 117 provides greater overall structural rigidity to sheath 24d in the event that endoscope 10 and sheath 24d are lifted. In addition, edges 119 of distal end member 110d provides support surfaces which rest upon underlying tissue and allow endoscope 10 and sheath 24d to remain in place with little or no support by the operator at handle 26.

Distal ends 110a–110d can be provided as a separate member permanently attached (e.g., soldered) to the end of the sheaths, as is the case for sheaths 24a–24c. Alternatively, as is the case with sheath 24d, distal end member 110d may be integrally-formed to the sheath.

In applications (e.g., SEPS), where gas insufflation is required at the surgical site, a cylindrical sheath 24e having a "closed" shaft 112e is provided. Sheath 24e communicates with gas port 59 in housing 16 to provide a supply channel for gas provided from insufflation source 46 (FIG. 1) through handle 26, housing 16 and through the cylindrical sheath. Because gas insufflation is relied upon to maintain a working space at the surgical worksite, sheath 24e does not require a flared distal end typical of open sheaths 24a–24d. In essence, sheath 24e creates a common working channel endoscope through which a wide variety of working surgical instruments can be introduced therethrough while allowing simultaneous viewing of the surgical worksite at the end of the sheath. The inner surface of closed sheath 24e also serves to guide the surgical instrument to the worksite. Distal end member 110e of sheath 24e also includes a longitudinal slot 121 which is used to provide simple dissection of tissue. For example, as sheath 24e is being advanced through tissue, veins which may require dissection are encountered. In these situations, slot 121 is used to peel away tissue surrounding the vein to determine, for example, whether the vein requires dissection.

Figure 11:
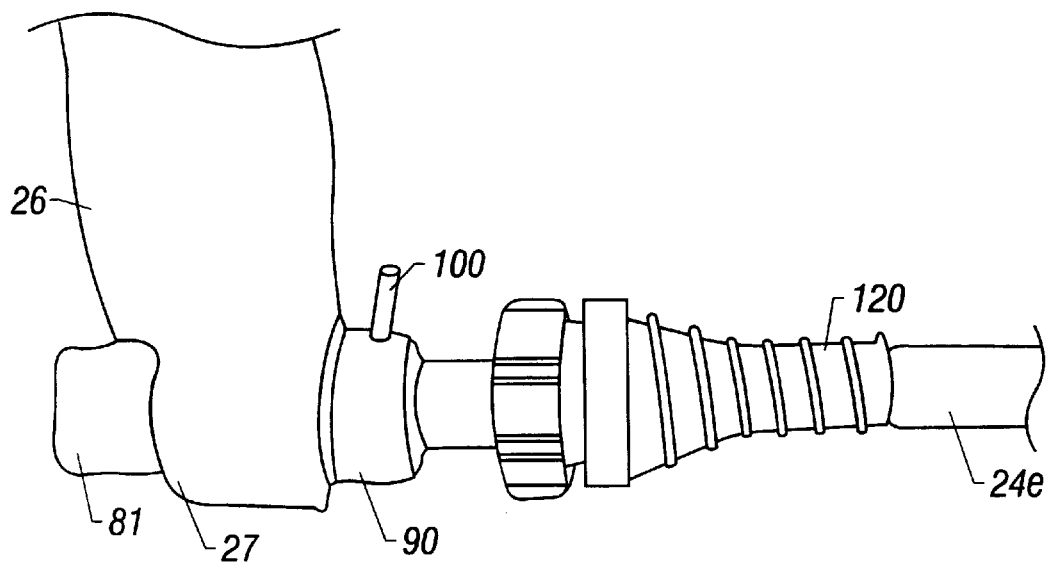
FIG. 11 is a side view of a portion of the endoscope of FIG. 1 having a closed sheath and gas seal attachment.

Referring to FIG. 11, a threaded seal 120 is slid over and positioned at the proximal end of closed sheath 24e. Seal 120 is secured in place using locking ring 122 and, in use, is threaded into incision port 12 to prevent escape of the gas from the incision port. Gas seal member 81 is placed over fitting 85 of housing 16 to provide an air-tight seal between a working instrument passing through working channel 18.

Referring again to FIG. 1, endoscope 10 having an open sheath 24 is shown in use in a procedure for harvesting a saphenous vein. Prior to placing endoscope 10 within incision port 12, a dissector 20 is used at incision port 12 to separate the fascia from the tissue. Dissection by direct visualization is generally limited to an area of only about 5 cm from incision port 12.

Figure 12:
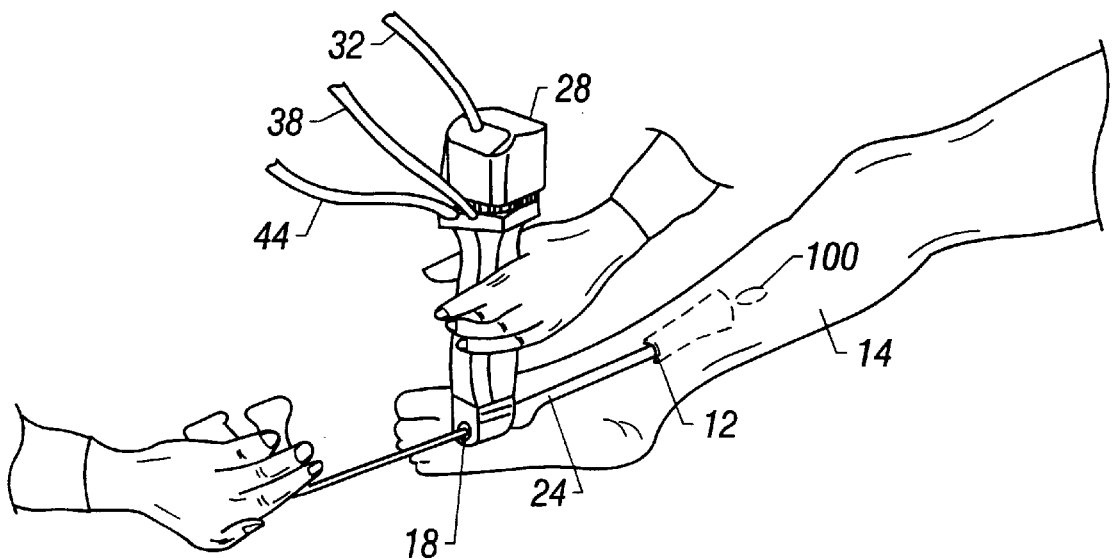
FIG. 12 shows the endoscope of FIG. 1 in use.

Referring to FIG. 12, after this initial dissection procedure, endoscope 10 with sheath 24 are inserted together through port 10 with the sheath held generally parallel to leg 14. Dissector 20 is then introduced through working channel 18 of endoscope 10 and separation of the fascia and tissue is continued with endoscope 10 used to visualize the dissection. Dissection continues in this manner, with sheath 24 maintaining a working space for dissector 20, until the surgical site is reached. In some surgical procedures, endoscope 10 is not required to be removed during this dissection procedure.

However, in other procedures, endoscope 10 may be used first with a detachable sheath 24 having a distal end member 110 with a relatively small cross-section (e.g., sheath 24d) to advance the endoscope to the target worksite. Upon arriving at the surgical worksite, endoscope 10 can be removed and a detachable sheath 24 having a larger distal end member (e.g., sheath 24a or 24b) can be used to temporarily displace tissue surrounding the worksite, thereby allowing better visualization of the worksite when a handheld instrument is passed through working channel 18 of endoscope. Alternatively, a larger sheath may be required to accommodate a different working instrument (e.g., ligator). In still other procedures, a closed detachable sheath (e.g., sheath 24e) may be exchanged for an open sheath and gas insufflation provided to displace tissue and expand the worksite.

Other embodiments and applications are within the claims. For example, although endoscope 10 is described as being useful for a saphenous vein harvesting procedure, it can be used in wide variety of surgical applications, including treatment of patients having incompetent perforating veins in a leg and suffering from chronic venous insufficiency.

In addition, use of endoscope 10 is not limited to vascular procedures, but has application in other surgical procedures where a working space needs to be maintained and simultaneous visualization is required. For example, endoscope 10 may be used to examine the thoracic cavity or to perform certain plastic surgical procedures.

What is claimed is:

1. An endoscope for internal inspection of an object comprising:
   a housing having a distal end and a working channel extending therethrough to the distal end, the working channel configured to allow passage of a surgical instrument;

an elongated insertion section having a proximal end mounted to the housing and a distal end to be inserted into the object, the elongated insertion section defining an optical axis of the endoscope; and a sheath, detachable from the housing distal end of the, and having a proximal end configured to be directly attached to the housing and a distal end, the sheath extending along the optical axis, covering a portion of the elongated insertion section, and defining a working space for the surgical instrument, the working space extending substantially from the proximal end of the sheath to the distal end of the sheath and communicating with the working channel of the housing, wherein a first portion of the working space occupied by the insertion section and a second portion of the working space occupied by the surgical instrument are contiguous with each other, the endoscope being configured to allow visualization, via the insertion section, of the surgical instrument inserted through the working channel and into the working space.

2. The endoscope of claim 1 wherein a distal end of the sheath is sized and shaped to temporarily displace portions of the object when inserted therein.

3. The endoscope of claim 2 wherein the distal end has a radius of curvature relative to the optical axis of the sheath greater than a radius of curvature of an elongated shaft portion of the sheath.

4. The endoscope of claim 3 wherein the distal end extends outwardly away from the optical axis.

5. The endoscope of claim 1 wherein the sheath defines an opening extending substantially the length of the sheath.

6. The endoscope of claim 5 wherein the opening defines a wall having in cross-section a C-shape.

7. The endoscope of claim 1 wherein the sheath is a tube surrounding the elongated insertion section.

8. The endoscope of claim 7 wherein the tube defines an insufflation channel extending through the housing.

9. The endoscope of claim 1 wherein the distal end of the housing has an outer surface configured to mate with a corresponding inner surface of a proximal end of the sheath.

10. The endoscope of claim 9 wherein the outer surface of the distal end of the housing and the inner surface of the proximal end of the sheath are tapered.

11. The endoscope of claim 10 further comprising a bayonet locking mechanism for mechanically coupling the sheath to the housing.

12. The endoscope of claim 10 further comprising a sealing ring positioned between an outer surface of the and for providing an airtight seal between the housing and sheath.

13. The endoscope of claim 1 further comprising a handle connected to the housing, the handle extending in a direction offset from the optical axis of the endoscope.

14. The endoscope of claim 13 wherein the handle extends in a direction substantially transverse to the optical axis of the endoscope.

15. The endoscope of claim 13 further comprising an optical system disposed within the elongated insertion section and extending through the handle.

16. The endoscope of claim 15 wherein the optical system includes a focusing mechanism and a rotatable manipulator coupled to the focusing mechanism.

17. The endoscope of claim 15 wherein the optical system includes a lens system to convey images of the object from a distal end of the insertion section to a proximal end of the insertion section.

18. The endoscope of claim 1 wherein the working channel has an exit port having a semi-circular shape.

19. The endoscope of claim 1 wherein the insertion section includes:

a light transmissive element for conveying light from an external light source to the object.

20. A method of visualizing a surgical procedure on a body comprising:

providing an endoscope including an elongated insertion section which defines an optical axis of the endoscope, the insertion section having a distal end to be inserted into the body; and a housing attached to a proximal end of the insertion section and having a distal end and a working channel extending therethrough to the end of the housing and substantially in parallel with the optical axis;

attaching a detachable sheath directly to the distal end of the housing, the sheath having a proximal end and a distal end on the housing so as to extend in parallel with the optical axis and cover a portion of the elongated insertion section, the sheath defining a working space extending substantially from the proximal end of the sheath to the distal end of the sheath, the working space communicating with the working channel of the housing;

positioning the insertion section and sheath through an incision port in the body and to a surgical worksite;

introducing a working instrument to the surgical worksite through the working channel of the housing into the working space, wherein a first portion of the working space occupied by the insertion section and a second portion of the working space occupied by the working instrument are contiguous with each other; and visualizing, via the insertion section, the working instrument at the surgical worksite after introduction through the working channel and into the working space.

21. The method of claim 20 wherein positioning the insertion section and sheath includes manipulating a handle attached to the housing and extending in a direction substantially transverse to the optical axis of the endoscope.

22. The method of claim 20 wherein manipulating the handle is performed using one hand of a user and introducing the working instrument is performed using the other hand of the user.

23. The method of claim 20 further comprising focusing the endoscope by actuating a focusing mechanism disposed on the handle.

24. The method of claim 20 further comprising introducing gas insufflation to the surgical worksite.

25. The method of claim 20 wherein the elongated insertion section includes a lens system to convey images of the object from a distal end of the insertion section to a proximal end of the insertion section.

* * * * *